(12) United States Patent
Bennett et al.

(10) Patent No.: US 9,650,654 B2
(45) Date of Patent: May 16, 2017

(54) MAKING C4+ PRODUCTS IN BACTERIA

(71) Applicant: WILLIAM MARSH RICE UNIVERSITY, Houston, TX (US)

(72) Inventors: George Bennett, Houston, TX (US); Chandresh Thakker, Houston, TX (US)

(73) Assignee: William Marsh Rice University, Houston, TX (US)

(*) Notice: Subject to any disclaimer, the term of this patent is extended or adjusted under 35 U.S.C. 154(b) by 0 days.

(21) Appl. No.: 14/749,372

(22) Filed: Jun. 24, 2015

(65) Prior Publication Data

US 2015/0376658 A1 Dec. 31, 2015

Related U.S. Application Data

(60) Provisional application No. 62/016,842, filed on Jun. 25, 2014.

(51) Int. Cl.
| | |
|---|---|
| *C12P 7/40* | (2006.01) |
| *C12P 7/04* | (2006.01) |
| *C12N 9/02* | (2006.01) |
| *C12P 7/16* | (2006.01) |
| *C12P 7/52* | (2006.01) |

(52) U.S. Cl.
CPC .............. *C12P 7/52* (2013.01); *C12N 9/0095* (2013.01); *C12P 7/04* (2013.01); *C12P 7/16* (2013.01); *C12P 7/40* (2013.01); *C12Y 118/01002* (2013.01); Y02E 50/10 (2013.01)

(58) Field of Classification Search
None
See application file for complete search history.

(56) References Cited

PUBLICATIONS

Chica et al. Curr Opin Biotechnol. Aug. 2005;16(4):378-84.*
Sen et al. Appl Biochem Biotechnol. Dec. 2007;143(3):212-23.*
Cai, X., et al., 2013. Analysis of redox responses during TNT transformation by Clostridium acetobutylicum ATCC 824 and mutants exhibiting altered metabolism. Appl Microbiol Biotechnol. 97(10):4651-4663.
Calusinska, M., et al., 2010. The surprising diversity of clostridial hydrogenases: a comparative genomic perspective. Microbiology. 156(6): 1575-1588.
Clark, S.W., at al., 1989. Isolation and characterization of mutants of Clostridium acetobutylicum ATCC 824 deficient in acetoacetyl-coenzyme A:acetate/butyrate:coenzyme A-transferase (EC 2.8.3.9) and in other solvent pathway enzymes. Appl. Environ Microbiol. 55 (4): 970-976.
Frigaard, N.U., et al., 2003. Chlorobium tepidum: insights into the structure, physiology, and metabolism of a green sulfur bacterium derived from the complete genome sequence. Photosynth Res. 78(2):93-117.
Girbal, L., et al., 2005. Homologous and heterologous overexpression in Clostridium acetobutylicum and characterization of purified clostridial and algal Fe-only hydrogenases with high specific activities. Appl. Environ Microbiol. 71(5):2777-2781.
Green, E.M., et al., 1996. Genetic manipulation of acid formation pathways by gene inactivation in Clostridium acetobutylicum ATCC 824, Microbiology, 142, 2079-2086.
Hillmann F, et al., 2008. PerR acts as a switch for oxygen tolerance in the strict anaerobe Clostridium acetobutylicum, Mol Microbiol. 68(4):848-60.
Hurley J.K., et al., 2002. Structure-function relationships in Anabaena ferredoxin/ferredoxin:NADP(+) reductase electron transfer: insights from site-directed mutagenesis, transient absorption spectroscopy and X-ray crystallography, Biochim Biophys Acta. 1554(1-2):5-21.
Peters, J.W., et al., 1998. X-ray crystal structure of the Fe-only hydrogenase (CpI) from Clostridium pasteurianum to 1.8 angstrom resolution. Science. 282(5395):1853-1858.
Peregrina J.R., et al., 2009. Motifs involved in coenzyme interaction and enzymatic efficiency in anabaena ferredoxin-NADP+ reductase. Biochemistry. 2009 48(14):3109-19.
Seo, D., Sakurai, H. 2002. Purification and characterization of ferredoxin-NAD(P)(+) reductase from the green sulfur bacterium Chlorobium tepidum. Biochim Biophys Acta. 1597 (1):123-132.
Seo, D., et al., 2001. Purification of ferredoxins and their reaction with purified reaction center complex from the green sulfur bacterium Chlorobium tepidum. Biochim Biophys Acta. 1503(3):377-384.
Tejero J. et al., 2003. Involvement of the pyrophosphate and the 2'-phosphate binding regions of ferredoxin-NADP+ reductase in coenzyme specificity, J Biol Chem. 278(49):49203-14.
Wagner C., et al., 1996. Acetogenic capacities and the anaerobic turnover of carbon in a kansas prairie soil, Appl. Environ. Microbiol. 62(2): 494-500.
Watrous, M.M., et al., 2003. 2,4,6-trinitrotoluene reduction by a Fe-only hydrogenase in Clostridium acetobutylicum. Appl. Environ Microbiol. 69(3):1542-1547.
Yoon, K.S., et al., 2001. Spectroscopic and functional properties of novel 2[4Fe-4S] cluster-containing ferredoxins from the green sulfur bacterium Chlorobium tepidum. J. Biol. Chem. 276(47):44027-44036.
Shen et al. 2011. Driving forces enable high-titer anaerobic 1-butanol synthesis in *Escherichia coli*. Appl Environ Microbiol. 77(9):2905-15.

* cited by examiner

*Primary Examiner* — Christian Fronda
(74) *Attorney, Agent, or Firm* — Boulware & Valoir

(57) ABSTRACT

Methods of making C4+ hydrocarbon feedstocks using anaerobic microbes are described.

14 Claims, 6 Drawing Sheets

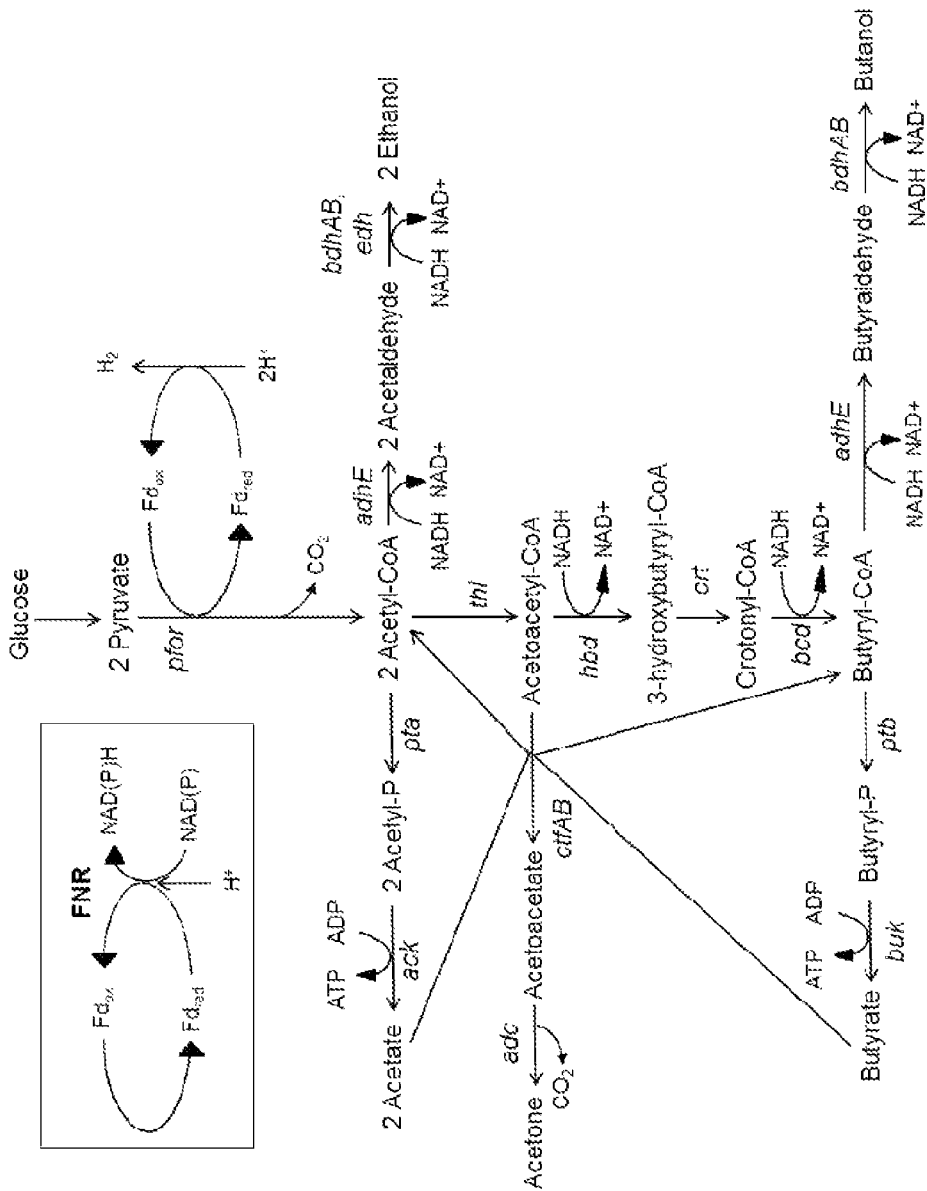
FIGURE 1: Metabolic pathways in *C. acetobutylicum*

Amino acid sequence of Ferredoxin–NADP reductase (FNR) of *Chlorobium tepidum* TLS (Genebank Accession Q8KCB2)

```
  1 mldihnpatd hhdmrdltii gggptgifaa fgcgmnnisc riiesmpgig gglaalypek
 61 hiydvagfpe vpaidlvesl wagaerynpd vvlnetvtky tklddgtfet rtntgnvyrs
121 ravliaaglg afeprklpql gnidhitgss vyyavksved fkgkrvvivg ggdsaldwtv
181 gliknaasvt lvhrghefgg hgktahever arangtidvy letevasiee sngvltrvhl
241 rssdgskwtv eadrlililg fksnlgplar wdlelyenal vvdshmktsv dglyaagdia
301 yypgklkiiq tglseatmav rhslsyikpg ekirnvfssv kmakekkaae agnatenkae
```

FIGURE 2A: SEQ ID NO.1

Codon optimized nucleotide sequence of FNR gene for expression in *Cl. acetobutylica* (1080 bp)

```
ATGTTAGATA
TCCATAATCC AGCAACCGAC CACCATGATA TGAGAGATTT GACTATTATC GGCGGTGGTC
CGACCGGGAT ATTTGCTGCC TTTCAATGTG GTATGAATAA CATATCATGC AGAATCATTG
AATCTATGCC TCAATTGGGT GGTCAACTTG CTGCACTATA TCCAGAAAAA CATATCTATG
ACGTTGCAGG ATTTCCCGAA GTTCCAGCTA TTGATTTGGT TGAGTCATTA TGGGCACAAG
CGGAAAGATA TAACCAGAGT GTCGTCCTTA ATGAAACAGT AACCAAGTAT ACCAAATTAG
ACGATGGGAC GTTTGAGACT AGAACCAATA CAGGTAATGT TTATCGATCA AGAGCTGTAC
TTATTGCAGC GGGATTAGGA GCATTTGAAC CACGTAAAACT TCCCCAATTA GGCAATATAG
ATCATCTAAC CGGTAGTTCT GTATACTATG CGGTTAAAAG CGTTGAAGAT TTCAAAGGTA
AAAGAGTTGT TATAGTCGGT GGTGGAGACA GCGCCTTAGA CTGGACCGTC GGACTTATCA
AAAATGCTGC ATCAGTAACA TTAGTGCACA GAGGACATGA ATTTCAAGGT CATGGTAAAA
CCGCCCATGA ATTTCCCGTT GCAAGAGCTA ATGGTACTAT TGATGTGTAT TTGGAAACAG
AGGTAGCAAG CATTGAAGAG TCTAATGGAG TATTAACTAG AGTTCATCTT AGATCAAGTG
ACGGTTCAAA GTGGACTGTT GAAGCGGATA GACTTCTTAT TCTAATAGGT TTTAAGTCAA
ACTTAGGTCC TTTAGCAAGA TGGGATTTAG AACTTTATGA AAATGCTTTA GTTGTTGATT
CTCACAATGA AACTTCCGTT GACGGACTTT ATGCTGCAGG AGACATTGCA TATTACCCGG
GGAAATTGAA AATCATACAG ACTGGGTTAT CAGAAGCGAC TATGGCTGTA AGGCATTCCC
TTAGTTATAT CAAACCTGGT GAGAAAATAC GTAACGTGTT CAGTTCCGTC AAGATGGCGA
AAGAAAAGAA AGCCGCAGAA GCTGGGAATG CTACTGAGAA TAAGGCTGAG
```

FIGURE 2B: SEQ ID NO. 2

Rbs: AGGAGGTAAAACAT

FIGURE 2C: SEQ ID NO. 3.

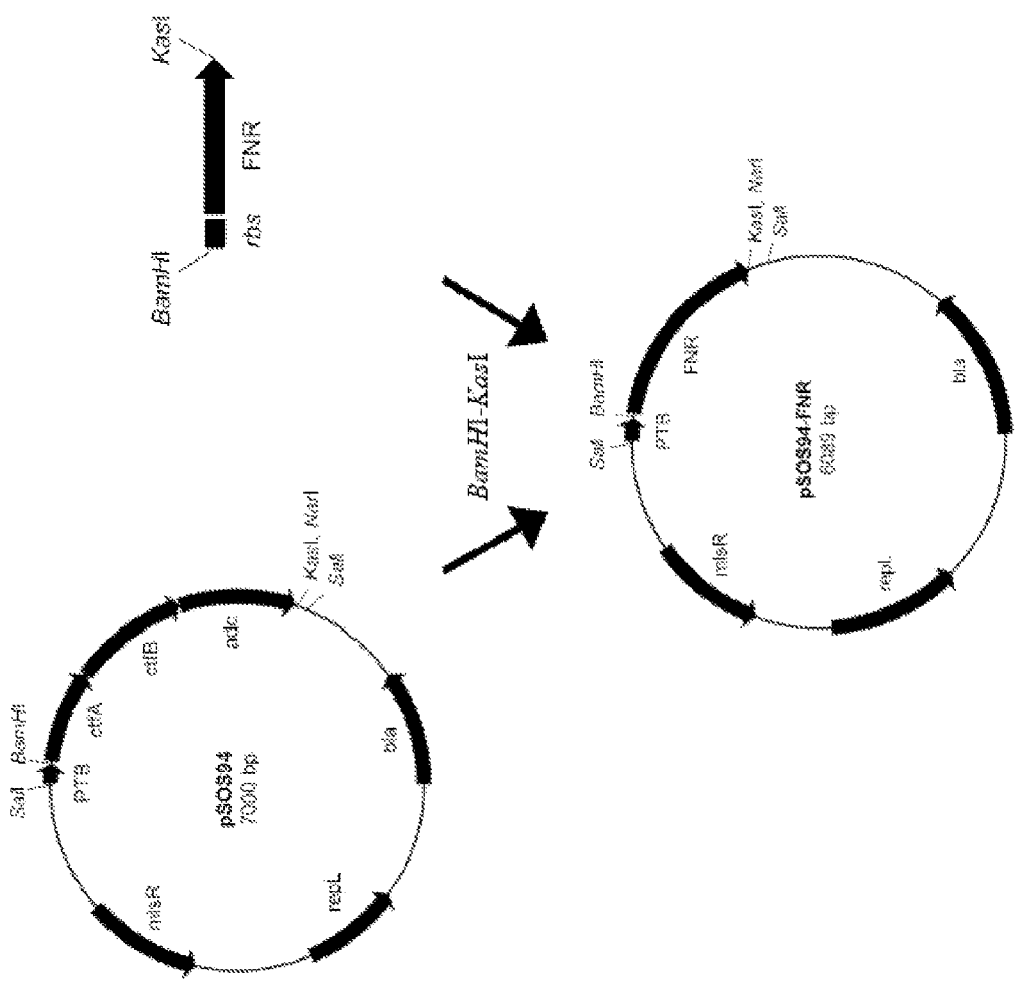
FIGURE 3: PLASMID MAPS

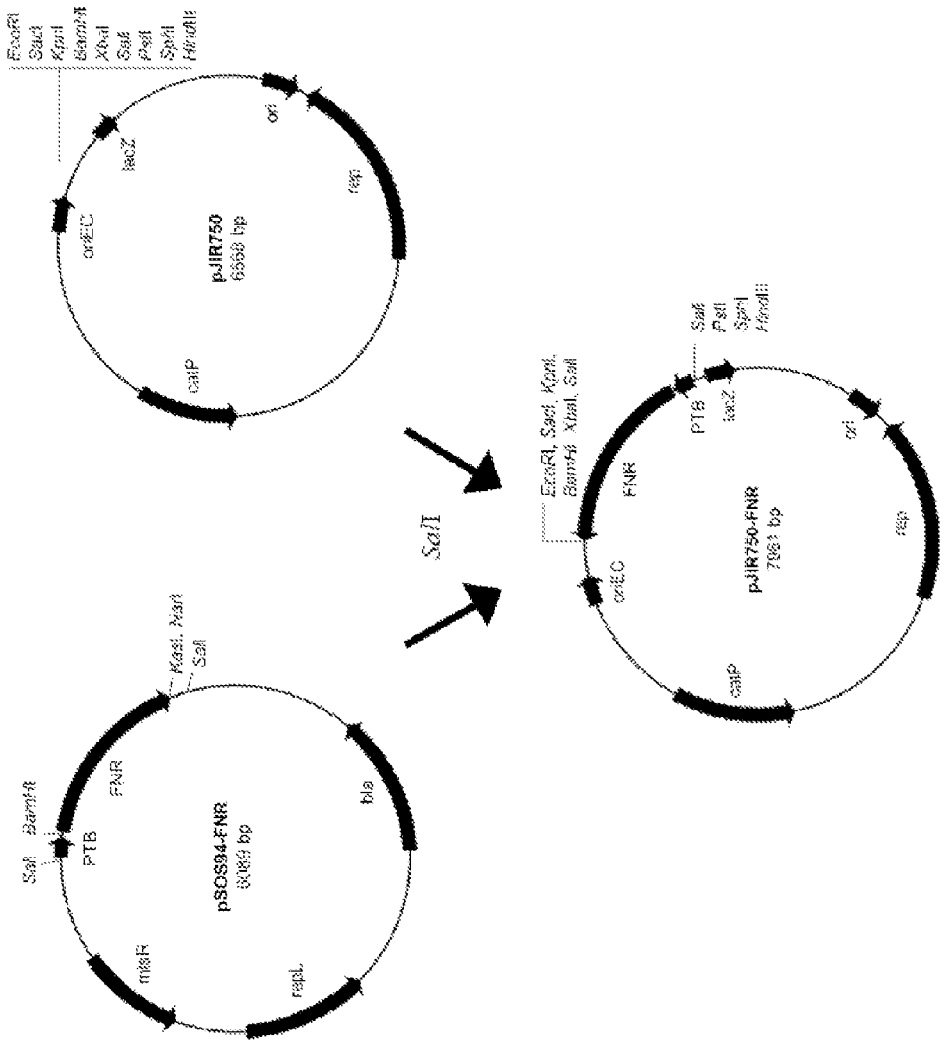
FIGURE 4: PLASMID MAPS

MAKING C4+ PRODUCTS IN BACTERIA

PRIOR RELATED APPLICATIONS

This Application claims priority to 62/016,842, filed Jun. 25, 2014, and incorporated by reference herein in its entirety for all purposes.

FEDERALLY SPONSORED RESEARCH STATEMENT

This invention was made with government support under CBET-1033552 awarded by the NSF. The government has certain rights in the invention.

FIELD OF THE DISCLOSURE

The disclosure generally relates to biological methods of making hydrocarbon feedstocks, in particular longer chain length organic acids and alcohols made in anaerobic microbes.

BACKGROUND OF THE DISCLOSURE

Four to ten carbon alkanes have many uses in our society, particularly as fuels and as feedstock for more complex chemicals. Most, however, are produced from petroleum, a dwindling reserve whose use creates significant ecological impact.

Butane (C4), for example, is mainly used for gasoline blending, as a fuel gas, either alone or in a mixture with propane, and as a feedstock for the manufacture of ethylene and butadiene, a key ingredient of synthetic rubber. Isobutane is primarily used by refineries to enhance the octane content of motor gasoline.

Very pure forms of butane, especially isobutane, can be used as refrigerants and have largely replaced the ozone layer-depleting halomethanes, for instance in household refrigerators and freezers. The system operating pressure for butane is lower than for the halomethanes, such as R-12, so R-12 systems such as in automotive air conditioning systems, when converted to butane will not function optimally.

Butane is also used as lighter fuel for a common lighter or butane torch and is sold bottled as a fuel for cooking and camping, and cordless hair irons are usually powered by butane cartridges.

In industry, hexanes (C6) are used in the formulation of glues for shoes, leather products, and roofing. They are also used to extract cooking oils from seeds, for cleansing and degreasing a variety of items, and in textile manufacturing. A typical laboratory use of hexanes is to extract oil and grease contaminants from water and soil for analysis. Since hexane cannot be easily deprotonated, it is used in the laboratory for reactions that involve very strong bases, such as the preparation of organolithiums, e.g. butyllithiums are typically supplied as a hexane solution. In many applications (especially pharmaceutical), the use of n-hexane is being phased out due to its long term toxicity, and often replaced by n-heptane, which will not form the toxic metabolite hexane-2,5-dione.

Octanes (C8) became well known in American popular culture in the mid- and late-sixties, when gasoline companies boasted of "high octane" levels in their gasoline advertisements. Thus, it too is useful in fuels. Decane (C10) undergoes combustion reactions in a similar fashion to other alkanes.

Thus, we can see that there are many important uses for low carbon number alkanes and the demand for C4+ alkanes is not expected to diminish any time soon. Yet as products of petroleum refining, the production of such alkanes contributes significantly to environmental degradation, and as our hydrocarbon resources continue to dwindle in availability, the alkanes can only be expected to increase in price over the long term.

There is also need for alcohols and acids of the C-4+ class such as butyrate, hexanoic acid, etc. and the corresponding alcohols that are used in many chemical processes. Chemical processes are known for interconversions among the C-4+ series of carbon compounds and used by the petrochemical industry, so a source of a particular reduced C-4+ compound can be useful for a variety of potential industrial processes.

Thus, what are needed in the art are biological sources for these important alkanes, and microbial production is being investigated in that regard. Unfortunately, not many bacteria make butane or hexane, at least not in significant amounts, and some of the bacteria that do are obligate anaerobes, which are difficult and expensive to culture.

Professor David Mullin, and his team have discovered a new bacteria, called Tu-103, a butane-producing bacteria that lives on glycerol—a byproduct of biodiesel synthesis, or on cellulose—a waste product in abundant supply from e.g., old newspapers. The microbe is unique because it can do this in the presence of oxygen, unlike some other types of bacterium, which means less expensive production techniques would be required than for most obligate anaerobes. However, little is known about this bacteria because details are being kept as a trade secret, and future patents may also prevent its use.

Nonetheless, the existence of such organisms has generated renewed interest in solventogenic bacteria, such as *Clostridia*, because it is anticipated that additional strains will be discovered that have some degree of tolerance to oxygen, removing some of the difficulties in using these organisms for the bioproduction of desired chemicals. Alternatively, increasing exposure to oxygen may induce some degree of oxygen tolerance, and/or random mutagenesis could result in such changes.

*Clostridium acetobutylicum*, for example, is an anaerobic, spore-forming prokaryote that produces the solvents butanol, acetone, and ethanol. The desired product of the *C. acetobutylicum* fermentation is butanol, which has superior fuel characteristics to ethanol, such as higher energy content and lower water miscibility. The *C. acetobutylicum* genome has been completely sequenced and annotated, and methods for genetic deletions and gene overexpression have been developed, making it even more attractive organism for further strain development. *Clostridia* can also grow on a variety of substrates, from simple pentoses and hexoses to complex polysaccharides.

The metabolism of *C. acetobutylicum* is typically biphasic in batch culture—the cells first produce acetate and butyrate, and later—butanol, acetone, and ethanol. During growth, the production of acids lowers the pH of the culture, which combined with butyrate accumulation causes a shift in metabolism towards solvent production.

As solvents are produced, the acids are typically re-assimilated and converted into solvents. With initiation of solvent formation, the cells commit to their sporulation program. In continuous culture or upon consecutive vegetative transfers, cells may degenerate whereby they become asporogenic and lose the capability to produce solvents. In this organism, the degeneration process is due to the loss of the pSOL1 megaplasmid, which carries the key solvent formation genes in the so-called sol locus made up of the sol operon (aad-ctfA-ctfB) (coding for the enzymes AAD and CoAT) and the adc gene (coding for the enzyme AADC, FIG. 5). The use of pSOL1 mutants can be beneficial in certain instances, reducing competition for carbon resources, and driving metabolism towards desired products.

What are needed in the art are additional methods of making C4-10 compounds using microbes. A method using some of the advantages of solventogenic bacteria, such as *Clostridia* may be of benefit as well.

SUMMARY OF THE DISCLOSURE

The present invention describes a method to capture redox by heterologous expression of ferredoxin NAD(P) reductase to allow the formation of longer chain organic acids and alcohols in anaerobic microbes.

To demonstrate proof of concept, we used ABE (acetone:butanol:ethanol) producing *Clostridium acetobutylicum* ATCC824, as well as a mutant variant strain M5 that has lost the mega plasmid pSOL1 (Clark et al. 1989) and a mutant variant strain PJC4BK, that is disrupted in buk, the gene encoding the major butyrate kinase.

As noted above, *C. acetobutylicum* displays two phase metabolism tightly associated with different growth stages. During the exponential growth, cells mainly produce acetic acid, butyric acid, $H_2$, ATP and NAD(P)H. In response to the acidic pH, the metabolism switches to solventogenesis wherein acids are re-consumed and acetone, butanol and ethanol produced to regenerate reducing equivalents.

A key enzyme of the *C. acetobutylicum* central metabolism is the pyruvate ferredoxin oxidoreductase (pfor, FIG. 1), which catalyzes the oxidative decarboxylation of pyruvate to produce acetyl-CoA, $CO_2$ and reduced ferredoxin. The reduced ferredoxin plays a key role as an electron carrier and is able, under appropriate conditions, to transfer electron to the iron hydrogenase for $H_2$ production. FIG. 1 shows the major genes whose encoded proteins catalyze that reaction are shown in the pathway diagram. In some cases there are more than one enzyme that acts in a particular reaction, however the major one or ones are indicated in the diagram.

To capture the lost redox via $H_2$ production, we used ferredoxin-NAD(P)+ reductase (FNR) (EC 1.18.1.3, 1.18.1.2) from the green sulphur bacterium *Chlorobium tepidum* TLS which is capable of efficiently catalyzing reduction of both NADP+ and NAD+, NAD+ being the more favorable, in the presence of reduced ferredoxin ($Fd_{red}$).

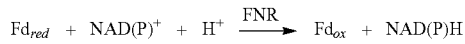

$$Fd_{red} + NAD(P)^+ + H^+ \xrightarrow{FNR} Fd_{ox} + NAD(P)H$$

where $Fd_{red}$=reduced ferredoxin and $Fd_{ox}$=oxidized ferredoxin

The 360 amino acid FNR protein encoding gene of *Chlorobium tepidum* was synthesized with a ribosome binding site (FIG. 2A-C) for the heterologous overexpression in *Clostridium acetobutylicum* strains ATCC824 and a degenerate strain (pSOL1⁻) M5 that cannot make acetone and butanol and buk⁻ mutant with butyrate kinase knockout. Heterologous expression of synthesized FNR in *Clostridia* catalyzes the transfer of electrons while recycling ferredoxin and reducing NAD+ to NADH and thereby captures the redox by minimizing $H_2$ production (FIG. 1, reaction in box).

This results in increase in NADH availability in vivo that is then channeled towards acetyl-CoA condensation and reduction to favor the formation of longer chain organic acids (such as butyric acid) and alcohols (such as butanol). The functionality of the newly introduced redox capturing ferredoxin enzyme was successfully demonstrated in anaerobic tube experiments performed in an anaerobic chamber. This increase in NADH availability significantly changed the final metabolite concentration pattern under anaerobic conditions.

We observed a change in metabolite pattern towards more butanol and less acetone in cultures of wild type *Clostridia* ATCC824, and more butyrate and less acetate in cultures of ATCC824 and M5 cells expressing FNR. The effect on the butyrate to acetate ratio was noticeable in ATCC824 cultures. During acidogenic stage (6 hr), the butyrate:acetate ratio was ~0.7-1.1 in wild type vector control (ATCC824 (pJIR750)) cultures; whereas, the butyrate:acetate ratio was ~1.6 for FNR⁺ (ATCC824(pJIR750-FNR)) cultures (Table 1).

Significant change was observed in the pattern of butanol and acetone in the cultures of ATCC824. In wild type ATCC824 cells grown to solvent stage, we observed an increase in the ratio of butanol:acetone from 1.46 in the parental strain with vector, ATCC824(pJIR750), to 2.8 in the culture of cells bearing the FNR⁺ plasmid pJIR750-FNR (Table 2). The pattern of acetone and butyrate changed significantly in the cultures of ATCC824(pJIR750-FNR). We also observed that in the solvent production stage of ATCC824(pJIR750-FNR) at 48 hr, levels of acetone decreased and butyrate increased as compared to wild type vector control cells ATCC824(pJIR750).

The effect on the ratio of butyrate to acetate was considerable in M5 (Table 3). After 6 hr, the typical butyrate:acetate ratio of ~1.14 was observed in control cultures of host M5 and M5(pJIR750) but in the strain M5(pJIR750-FNR) expressing the ferredoxin NAD(P) reductase the ratio was ~2.8, and after 24 hr culture the ratios were 1.85 in the M5 cultures and 3.7 in the M5 FNR⁺ cultures (Table 3). These results indicate the added enzyme can divert redox to NADH and generate a more reduced pattern of metabolites, such as butyrate and butanol.

In the buk⁻ mutant strain expressing pJIR750 or pJIR750-FNR, the levels of acetone, ethanol, acetate and butyrate were significantly different. In cultures of buk⁻ fnr⁺ at 48 hr, the levels of acetone, acetate, butyrate and ethanol dropped to about 33%, 50%, 50% and 11%, respectively. The buk⁻ (pJIR750-FNR) strain showed about 6% increase in butanol concentration at 48 hr as compared to buk⁻ (pJIR750) vector alone strain. These changes were more significant in terms of butanol:acetone, total solvent/acid ratios and percent butanol of total solvents on gram basis.

The butanol:acetone ratio for buk⁻ (pJIR750) were 1.5 and 2 as compared to 2.2 and 3.2 for buk⁻ (pJIR750-FNR) at 24 and 48 hr, respectively. The solvent:acid ratio for buk⁻ (pJIR750) were 8.4 and 7.8 as compared to 11.7 and 13.9 for buk⁻ (pJIR750-FNR) at 24 and 48 hr, respectively. The percent butanol of total solvents on gram basis for buk⁻ (pJIR750) was 56 and 60 as compared to 63 and 68 for buk⁻ (pJIR750-FNR) at 24 and 48 hr, respectively.

In summary, the advantages and features of using an overexpressed ferredoxin-NAD(P) oxidoreductase include:

1. Capturing of redox which is otherwise used in the production of hydrogen and thereby increased availability of NADH.

2. Increased NADH levels in vivo results in formation of NADH dependent metabolites such as longer chain organic acid butyrate over acetate and butanol over acetone.

3. Enhanced yield of butyrate.

The experiments herein show that the proportion of butanol and butyrate is increased in the presence of the FNR gene encoded by *C. tepidium*. There are also FNR genes from plants and cyanobacteria and *Plasmonium falciparum* ferredoxin-NADP+ reductase that could be used in the invention. Most of those show a high preference for NADPH. Additionally, quite a bit of work has been done on the *Anabaena* enzyme, and it is also a useful enzymes for use hereunder.

One way to find other enzymes that can be used in the invention is by BLAST search of amino acid homologs:

| UniProt | Species | % AA identity |
|---------|---------|---------------|
| Q8KCB2 | *Chlorobium tepidum* | 100.0% |
| B3QPZ8 | *Chlorobaculum parvum* | 90.8% |
| A1BHP4 | *Chlorobium phaeobacteroides* | 76.6% |
| B4SFQ3 | *Pelodictyon phaeoclathratiforme* | 76.6% |
| Q0YS49 | *Chlorobium ferrooxidans* | 75.7% |
| Q3AS18 | *Chlorobium chlorochromatii* | 75.5% |
| B3EEF0 | *Chlorobium limicola* | 74.3% |
| A4SFT9 | *Prosthecochloris vibrioformis* | 74.9% |
| Q3B2Q8 | *Pelodictyon luteolum* | 73.5% |
| B4S9F8 | *Prosthecochloris aestuari* | 71.6% |

Other FNR enzymes that might be used herein include those listed below, but typically several hundred are provided at e.g., UniProt or Brenda and other databases by protein name, gene name, by homology or by EC number.

| EC 1.18.1.2 - ferredoxin-NADP+ reductase | | |
|---|---|---|
| Synonym | Species | UniProt Acc. No. |
| ABO_0145 | *Alcanivorax borkumensis* | Q0VTC7 |
| ferredoxin-NADP+ oxidoreductase | *Arabidopsis thaliana* | Q8W493 F4JZ46 Q9FKW6 |
| ferredoxin-NADP+ oxidoreductase | *Bacillus subtilis* | O05268 |
| FNR1 | *Chlamydomonas reinhardtii* | A8J6Y8 |
| ferredoxin:NADP+ reductase | *Cryptosporidium parvum* | Q5CVU8 |
| ferredoxin-NADP+ reductase | *Escherichia coli* | P28861 |
| PETH | *Nostoc* sp. ATCC 29151 | P21890 |
| PETH | *Pisum sativum* | P10933 |
| FprA | *Pseudomonas putida* | T2HBT5 |
| ferredoxin (flavodoxin)-NADP(H) reductase | *Rhodobacter capsulatus* | Q9L6V3 |
| FNR | *Synechococcus elongatus* | Q93RE3 |
| ferredoxin NADP+ oxidoreductase | *Triticum aestivum* | Q8RVZ8 Q8RVZ9 |
| PETH | *Synechocystis* sp. | Q55318 |
| ST2133 | *Sulfolobus tokodaii* | Q96YN9 |
| FNR | *Zea mays* | Q9SLP6 |
| FNR | *Xanthomonas axonopodis* | Q8PMH0 |
| FNR | *Chlamydomonas reinhardtii* | A8J6Y8 |
| ferredoxin--NADP(+) reductase | *Anabaena variabilis* | CAA37973 (GenBank) WP_011317640.1 (GenBank) |
| Ferredoxin--NADP(+) reductase | *Anabaena cylindrica* | AFZ57822 (GenBank) |
| ferredoxin--NADP reductase | *Nostoc* sp. PCC 7120 | WP_010998260.1 |

| EC 1.18.1.3 - ferredoxin-NAD+ reductase | | |
|---|---|---|
| Synonym | Uniprot | Species. |
| Rnf | D8GR70 | *Clostridium ljungdahlii* |
| D3P0M6 | D3P0M6 | *Halorhabdus tiamatea* SARL4B |
| Ferredoxin--NAD(P)(+) reductase fdr (EC 1.18.1.2) (EC 1.18.1.3) (Carbazole 1,9a-dioxygenase, ferredoxin reductase component) (CARDO) | D5IGG6 | *Sphingomonas* sp. |
| Ferredoxin--NAD(+) reductase (EC 1.18.1.3) | F4CQP8 | *Pseudonocardia dioxanivorans* |
| Ferredoxin--NAD(+) reductase GenePsed_1526 | F4CU45 | *Pseudonocardia dioxanivorans* |
| Ferredoxin--NAD+ reductase protein (EC 1.18.1.3) (Ni/Fe hydrogenase, gamma subunit) | F7PL38 | *Halorhabdus tiamatea* SARL4B |
| Ferredoxin--NAD(+) reductase (EC 1.18.1.3) | P24134 | *Streptomyces griseus* |
| Ferredoxin--NAD(P)(+) reductase CarAd (EC 1.18.1.2) (EC 1.18.1.3) (Carbazole 1,9a-dioxygenase, ferredoxin reductase component) (CARDO) | Q8GI14 | *Pseudomonas resinovorans* |

Each of Initial cloning experiments sometimes proceed in *E. coli* for convenience since most of the required genes are already available in plasmids suitable for expression in *E. coli*, but the addition of genes to bacteria is of nearly universal applicability, so it will be possible to use a wide variety of organisms with the selection of suitable vectors for same. Furthermore, a number of databases include vector information and/or a repository of vectors. See e.g., Addgene.org which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues.

The enzymes can be added to the genome or on expression vectors, as desired. Preferably, multiple enzymes are expressed in one vector or multiple enzymes can be combined into one operon by adding the needed signals between coding regions. Further improvements can be had by overexpressing one or more, or even all of the enzymes, e.g., by adding extra copies to the cell via plasmid or other vector. Initial experiments will employ expression plasmids hosting 3 or more ORFs for convenience, but it may be preferred to insert operons or individual genes into the genome for stability reasons.

Still further improvements in yield can be had be removing competing pathways, such as those pathways for making e.g., acetate, and it is already well known in the art how to reduce or knockout these pathways. Our own lab has several patent applications addressing such improvements, and such hosts may also make suitable starting materials since they are already available.

Generally speaking, we have referenced protein names herein and included EC numbers for accurate identification, but it is understood that a change in protein activity can of course be effected by changing the gene. This provides clarity since the gene nomenclature can be widely divergent in bacteria, but the proteins are defined by their activities and EC numbers.

Once an exemplary protein is obtained, e.g., in *E. coli*, which is completely sequenced and which is the workhorse of genetic engineering and bioproduction, many additional examples proteins of similar activity can be identified by BLAST search or database search. Further, every protein record is linked to a gene record, making it easy to design overexpression vectors. Many of the needed enzymes are already available in vectors, and can often be obtained from cell depositories or from the researchers who cloned them. But, if necessary, new clones can be prepared based on available sequence information using RT-PCR techniques. Thus, it should be easily possible to obtain all of the needed enzymes for overexpression, and in fact, we already have several clones, and are collecting the rest.

Understanding the inherent degeneracy of the genetic code allows one of ordinary skill in the art to design multiple nucleotides that encode the same amino acid sequence. NCBI™ provides codon usage databases for optimizing DNA sequences for protein expression in various species. Using such databases, a gene or cDNA may be "optimized" for expression in *E. coli* or *Clostridia* or other bacterial species using the codon bias for the species in which the gene will be expressed.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250. The default parameters were used, except the filters were turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 1 1 for proteins; E Cost to extend gap [Integer] default=2 for nucleotides, 1 for proteins; q Penalty for nucleotide mismatch [Integer] default=−3; r reward for nucleotide match [Integer] default=1; e expect value [Real] default=10; W word size [Integer] default=1 1 for nucleotides, 3 for proteins; y Dropoff (X) for blast extensions in bits (default if zero) default=20 for blastn, 7 for other programs; X dropoff value for gapped alignment (in bits) 30 for blastn, 15 for other programs; Z final X dropoff value for gapped alignment (in bits) 50 for blastn, 25 for other programs. This program is available online at NCBI™ (ncbi.nlm.nih.gov/BLAST/).

As used herein the specification, "a" or "an" may mean one or more. As used herein in the claim(s), when used in conjunction with the word "comprising", the words "a" or "an" may mean one or more than one. As used herein "another" may mean at least a second or more.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

As used herein, the expressions "cell", "cell line" and "cell culture" are used interchangeably and all such designations include progeny. Thus, the words "cells" and similar designations include the primary subject cell and cultures derived therefrom without regard for the number of transfers. It is also understood that all progeny may not be precisely identical in DNA content, due to deliberate or inadvertent mutations that arise after genetic engineering is concluded. Mutant progeny that have the same function or biological activity as screened for in the originally transformed cell are included. Where distinct designations are intended, it will be clear from the context.

The terms "operably associated" or "operably linked," as used herein, refer to functionally coupled nucleic acid sequences.

As used herein "recombinant" is relating to, derived from, or containing genetically "engineered" material. In other words, the genome was intentionally manipulated by the hand of man in some way.

"Reduced activity" or "inactivation" is defined herein to be at least a 75% reduction in protein activity, as compared with an appropriate control species. Preferably, at least 80, 85, 90, 95% reduction in activity is attained, and in the most preferred embodiment, the activity is eliminated (100%). Proteins can be inactivated with inhibitors, by mutation, or by suppression of expression or translation, and the like. A negative superscript, as in buk$^-$, indicates reduced activity.

"Overexpression" or "overexpressed" is defined herein to be at least 150% of protein activity as compared with an appropriate control species. If the gene/protein of is not available in the host species, any expression is overexpression. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like. An overexpressed protein can be represented by the + symbol, e.g., FNR$^+$.

As used herein "100% anaerobic" refers to those conditions of zero oxygen such that obligate anaerobes can grow. Anaerobic by contrast, may allow some very low degree of oxygen, such that anaerobes with some degree of oxygen tolerance can grow. It is now known that obligately anaerobic bacteria such as acetogenic bacteria are stable to periods of aerobiosis. See Wagner (1996).

The terms "disruption" as used herein, refer to cell strains in which the native gene or promoter is mutated, deleted, interrupted, or down regulated in such a way as to decrease the activity of the protein at least 90% over the wild type un-disrupted protein. A gene or protein can be completely (100%) reduced by knockout or removal of the entire genomic DNA sequence. A knockout mutant can be represented by the Δ symbol.

Use of a frame shift mutation, early stop codon, point mutations of critical residues, or deletions or insertions, and the like, can completely inactivate (100%) gene product by completely preventing transcription and/or translation of active protein.

The following abbreviations, plasmids and strains are used herein:

| ABBREVIATION | FULL NAME |
|---|---|
| FNR | ferredoxin-NAD(P)$^+$ reductase (EC 1.18.1.3, 1.18.1.2), sometimes called ferredoxin-NAD(P)$^+$ oxidoreductase |
| YTG | Yeast tryptone glucose medium, often used for clostridia |
| CGM | Clostridial growth medium; KH$_2$PO$_4$, 0.75 g; K$_2$HPO$_4$, 0.75 g; MgSO$_4$•H$_2$O, 0.4 g; MgSO$_4$•H$_2$O, 0.01 g; FeSO$_4$•7H$_2$O, 0.01 g; NaCl, 1.0 g; asparagine, 2.0 g; yeast extract, 5.0 g; (NH$_4$)$_2$SO$_4$, 2.0 g; and carbohydrate, 5 g |
| 2x YTG | pH 5.8; 16 g Bacto tryptone, 10 g yeast extract, 4 g NaCl, and 113 5 g glucose per L |
| PTB | phosphotransbutyrylase promoter |
| ctfA | acetoacetyl-CoA:acetate/butyrate:CoA transferase subunit A |
| ctfB | acetoacetyl-CoA:acetate/butyrate:CoA transferase subunit B |
| adc | acetoacetate decarboxylase |
| bla | beta-lactamase for ampicillin resistance; repL, replication protein |
| mlsR | macrolide-lincosamide-streptogramin B resistance protein |
| repL | replication protein |
| mlsR | macrolide-lincosamide-streptogramin B resistance protein |
| lacZ | beta-galactosidase alpha-peptide; |
| ori | *C. perfringens* pIP404 replication origin; |
| rep | replication enzyme |
| catP | chloramphenicol acetyltransferase |
| oriEC | replication region |
| OD | Optical density |
| TH20 | Thiamphenicol 20 μg/ml |

DESCRIPTION OF DRAWINGS

FIG. 1. Metabolic pathways in *C. acetobutylicum*. Ferredoxin NAD(P) reductase (FNR) catalyzed reaction of utilizing redox while reducing NAD(P) to NAD(P)H is shown in the box. pfor: pyruvate ferredoxin oxidoreductase; ack: acetate kinase; pta: phosphate acetyltransferase; adhE: aldehyde alcohol dehydrogenase; bdhAB: butanol dehydrogenase; edh: ethanol dehydrogenase; thl: acetoacetyl-CoA thiolase; hbd: 3-hydroxybutyryl-CoA dehydrogenase; adc: acetoacetate decarboxylase; ctfAB: butyrate-acetoacetate CoA-transferase; crt: 3-hydroxybutyryl-CoA dehydratase; bcd: butyryl-CoA dehydrogenase; ptb: phosphotransbutyrylase; buk: butyrate kinase.

FIG. 2A SEQ ID NO. 1 Amino acid sequence of native Ferredoxin-NAD(P) reductase (FNR) of *Chlorobium tepidum* TLS (GenBank Accession Q8KCB2), and FIG. 2B SEQ ID NO. 2. Optimized nucleotide sequence of FNR for expression in *Clostridium acetobutylicum* ATCC 824. FIG. 2C SEQ ID NO. 3. Synthetic ribosome binding site.

FIG. 3. Plasmid Maps: Schematic diagram showing the construction of pSOS94-FNR. The 1.1 Kb FNR (Ferredoxin-NAD(P) reductase) of *Chlorobium tepidum* TLS was codon optimized for expression in *Clostridium acetobutylicum*, synthesized with ribosome binding site (rbs), and cloned in pSOS94 using BamHI and KasI sites. The newly constructed ~6.1 Kb pSOS94-FNR expresses the FNR under constitutive PTB promoter. Abbreviations: PTB, phosphotransbutyrylase promoter; ctfA, acetoacetyl-CoA:acetate/butyrate:CoA transferase subunit A; ctfB, acetoacetyl-CoA:acetate/butyrate:CoA transferase subunit B; adc, acetoacetate decarboxylase; FNR, codon optimized ferredoxin-NADP reductase gene from *C. tepidum*; bla, beta-lactamase for ampicillin resistance; repL, replication protein; mlsR, macrolide-lincosamide-streptogramin B resistance protein. Restriction enzyme sites: BamHI, KasI, NarI, SalI.

FIG. 4. Plasmid Maps: Schematic diagram showing the construction of pJIR750-FNR. The ~1.4 Kb fragment containing PTB promoter, ribosome binding site and codon optimized FNR (Ferredoxin-NADP reductase) of *Chlorobium tepidum* TLS was excised from pSOS94-FNR using restriction enzyme SalI, and ligated to SalI digested ~6.6 Kb pJIR750. The newly constructed 7.9 Kb pJIR750-FNR expresses the FNR under constitutive PTB promoter. Abbreviations: PTB, phosphotransbutyrylase promoter; FNR, codon optimized ferredoxin-NADP reductase gene from *C. tepidum*; bla, beta-lactamase for ampicillin resistance; repL, replication protein; mlsR, macrolide-lincosamide-streptogramin B resistance protein; lacZ, beta-galactosidase alpha-peptide; ori, *C. perfringens* pIP404 replication origin; rep, replication enzyme; catP, chloramphenicol acetyltransferase; oriEC, replication region. Restriction enzyme sites: BamHI, KasI, NarI, SalI, EcoRI, SacI, KpnI, XbaI, PstI, SphI, HindIII.

DETAILED DESCRIPTION

Figure 5:
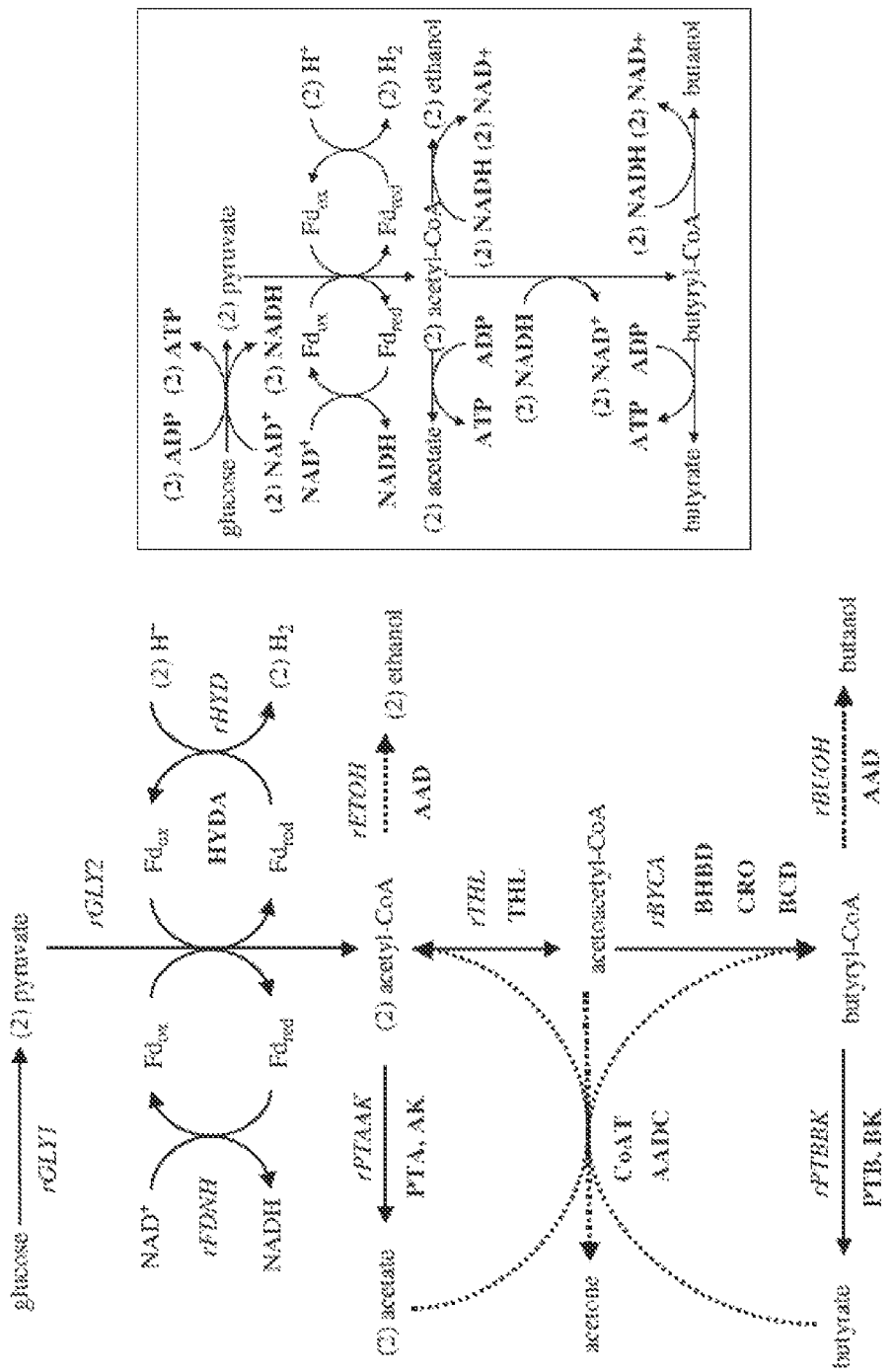
FIG. 5. *C. acetobutylicum* pathways and pSOL1 genes. Metabolic pathways in *C. acetobutylicum* and associated calculated in vivo fluxes. Selected enzymes are shown in bold and associated intracellular fluxes are shown in italics. Enzymes are abbreviated as follows: hydrogenase (HYDA); phosphotransacetylase (PTA); acetate kinase (AK); thiolase (THL); β-hydroxybutyryl dehydrogenase (BHBD); crotonase (CRO); butyryl-CoA hydrogenase (BCD); CoA Transferase (CoAT); acetoacetate decarboxylase (AADC); butyrate kinase (BK); phosphotransbutyrylase (PTB); alcohol/aldehyde dehydrogenase (AAD). Note: AAD is believed to be the primary enzyme for butanol and ethanol formation but additional genes exist that code for alcohol forming enzymes (adhe2, bdhA, bdhB, CAC3292, CAP0059) The pathways whose genes reside on the pSOL1 megaplasmid and are absent in M5 are shown as dotted lines. The boxed pathway shows the ATP generation and NADH production occurring during metabolism.

The disclosure relates to bacteria for making C4+ organic acids, alcohols or derivatives thereof, as well as to methods of making C4+ organic acids, alcohols or derivatives therefrom by culturing the engineered bacteria described herein with a source of carbon, forming C4+ organic acids, alcohols or derivatives, harvesting said C4+ products. The products can be used as is, or converted to other desirable compounds such as alkanes, alkenes, alcohols, esters, acids, amides, and the like.

Preferred compounds made herein include the saturated C4-C8 acids (or esters thereof):

| Butyric acid | Butanoic acid | $CH_3(CH_2)_2COOH$ | C4:0 |
| Valeric acid | Pentanoic acid | $CH_3(CH_2)_3COOH$ | C5:0 |
| Caproic acid | Hexanoic acid | $CH_3(CH_2)_4COOH$ | C6:0 |
| Enanthic acid | Heptanoic acid | $CH_3(CH_2)_5COOH$ | C7:0 |
| Caprylic acid | Octanoic acid | $CH_3(CH_2)_6COOH$ | C8:0 |
| Pelargonic acid | Nonanoic acid | $CH_3(CH_2)_7COOH$ | C9:0 |

Other preferred products include the alcohols, butanol, pentanol, hexanol, heptanol and octanol.

Preferably, the above bacteria also have reduced fermentation pathways leading to competing products, such as acetate, lactate, ethanol and/or formate. Many such mutants are already available in the art and can be used as host cells, or the vectors can be used to introduce same.

Acetogens are a useful starting host, as they may contain one or more of the required enzymes (e.g., certain bacteria contain an enzyme for reaction 6), and be suitable for making C4-8 or C4-10 products. Most acetogens use the "Wood-Ljungdahl" pathway. The Wood-Ljungdahl pathway is a set of biochemical reactions used by some bacteria and archaea. It is also known as the reductive acetyl-CoA pathway, and enables certain organisms to use hydrogen as an electron donor and carbon dioxide as an electron acceptor as well as a building block for biosynthesis. In this pathway carbon dioxide is reduced to carbon monoxide, which is then converted to acetyl coenzyme A. Two enzymes participate, CO Dehydrogenase and acetyl-CoA synthase. The former catalyzes the reduction of the $CO_2$ and the latter combines the resulting CO with a methyl group to give acetyl-CoA. Unlike the Reverse Krebs cycle and the Calvin cycle, this process is not cyclic.

Many acetogens are thought to be strict anaerobes, thus it may be preferred to perform some of the needed engineering in a more easily grown bacteria, such as *E. coli*, or other commonly engineering microbe. However, acetogens are also present in aerated soils and colonize habitats with fluctuating redox conditions (e.g., the rhizosphere of sea grass), suggesting that less strict isolates are obtainable, as confirmed by Mullin's work. The use of anaerobes that are less strict may be preferred as maintaining 100% anaerobic conditions is difficult and costly.

Other acetogens include *Clostridium autoethanogenum, Eurobacterium limosum, Clostridium carboxidivorans P7, Peptostreptococcus* products, and *Butyribacterium methylotrophicum, Clostridium ljungdahlii* and *Acetobacterium woodii*.

Still other bacteria that could be useful hosts include *Clostridium, Butyrobacterium, Moorella thermoacetica, Sporomusa, Thermacetogenium phaeum, Clostridium thermocellum, Acetogenium kivui, Acetobacterium woodii, Butyribacterium methylotrophicum, Clostridium ljungdahlii, Clostridium thermoautotrophicum, Clostridium tyrobutyricum,* or *Eubacterium limosum,* or any other organism that uses ferredoxin as a major means of electron transfer factor.

In more detail, the invention includes one or more of the following embodiments in any combination thereof:

A genetically engineered bacteria, comprising an overexpressed ferredoxin-NAD(P)+ reductase (FNR) capable of catalyzing reduction of either NADP+ or NAD+ or both, said bacteria able to anaerobically produce more C4-8 organic acids or alcohols than a similar bacteria lacking said overexpressed FNR.

A genetically engineered acetogenic bacteria, comprising an overexpressed heterologous ferredoxin-NAD(P)+ reductase (FNR) capable of efficiently catalyzing reduction of both NADP+ and NAD+, said bacteria able to anaerobically produce more C4-C8 organic acids or alcohols than a similar bacteria lacking said overexpressed heterologous FNR.

A genetically engineered Clostridial bacteria, comprising an overexpressed heterologous ferredoxin-NAD(P)+ reductase (FNR) capable of efficiently catalyzing reduction of both NADP+ and NAD+, said bacteria able to anaerobically produce more C4-C8 organic acids or alcohols than a similar bacteria lacking said overexpressed heterologous FNR.

A bacteria as described herein, wherein said FNR is a heterologous FNR.

A bacteria as described herein, further comprising a mutation such that said bacteria cannot make acetone, lactate, formate or combinations thereof A bacteria as described herein, wherein said bacteria is an acetogenic bacteria.

A bacteria as described herein, wherein said bacteria is a *Clostridium, Clostridium acetobutylicum, Clostridium acetobutylicum* M5, *Clostridium thermocellum, Clostridium ljungdahlii, Clostridium thermoautotrophicum,* or *Clostridium tyrobutyricum*.

A bacteria as described herein, wherein said bacteria is a *Butyrobacterium, Moorella thermoacetica, Sporomusa, Thermacetogenium phaeum, Acetogenium kivui, Acetobacterium woodii,* or *Eubacterium*.

A bacteria as described herein, The bacteria of claim 1, wherein said bacteria is *Clostridium acetobutylicum* M5.

A method for the bioproduction of a C4+ compound, said method comprising:
   anaerobically growing a bacteria as described herein in a culture medium comprising a carbon source;
   conversion of said carbon source to a C4+ compound; and
   purification of said C4+ compound.

A method as herein described, wherein said C4+ compound is butyrate, butanol, valeric acid, pentanol, hexanoate, hexanol, heptanoate, heptanol, octanoate, octanol, or a derivative thereof, and is preferably, butyrate, butanol or derivatives thereof A method as herein described, wherein said growing step is anaerobic.

A method as herein described wherein said growing step is 100% anaerobic.

A method as herein described, wherein said growing step is <100% anaerobic, e.g., the bacteria is not a strict anaerobe. Such bacteria can be selected for some degree of oxygen tolerance before or after the genetic engineering step.

Materials and Methods

Experiments were performed in anaerobic glove box containing 85% $N_2$, 10% $H_2$ and 5% $CO_2$ atmosphere. Glycerol stocks of *C. acetobutylicum* ATCC 824 and its mutant strain M5 (Clark 1989) harboring pSOS94-FNR (FIG. 3) or pJIR750-FNR (FIG. 4) were streaked on 2×YTG and incubated at 37° C. for 2-5 days. Preculture was prepared by inoculating a single colony from 2×YTG plate in 10 mL of CGM+ containing 25 mg/L thiamphenicol or 40 mg/L erythromycin in 15 mL falcon tube and incubated at 37° C. for 14-16 h. 200 μL of preculture was used as inoculum for fermentation experiments performed in 15 mL tubes with loose cap containing 10 mL CGM+ with 50 g/L glucose at 37° C. without shaking.

Samples were collected at various time points to measure OD600 and metabolites. 1 mL sample was centrifuged at 12,000 rpm for 5 min at room temperature to remove cell debris and clear supernatant was acidified with 20 μL 50% $H_2SO_4$. Metabolites such as ethanol, acetone, acetic acid, butanol and butyric acid were measured by gas chromatography equipped with FID detector and PoraPak™ QS 80/100 glass column.

In the Tables below, ATCC824 is wild type *Clostridium acetobutylicum*. M5 is a pSOL1⁻ mutant strain of the same bacterium. This mutant is used to show that the redistribution of redox from reduced Fd can generate longer chain acids in the metabolite profile of an acidogenic culture, and would be similar to the acidigenic metabolites produced by *Clostridium tyrobutyricum* or *clostridium butyricum*, as an example of the effect on a non-solvent producing *clostridium* species. The A and B refer to different isolates from the same transformation.

pJIR750 is a *Clostridium perfringens-Escherichia coli* shuttle vector derived from pJIR418 (ATCC 77387) permitting expression of antibiotic resistance (chloramphenicol resistance (catP)) in both hosts. pJIR750-FNR contains a codon optimized gene for FNR (SEQ ID NO. 2).

TABLE 1 butyrate/acetate ratio of wild type *C. acetobutylicum* with or without FNR from *Chlorobium tepidium*

| Strain | Butyrate:Acetate ratio 6 h | 24 h | 48 h | 72 h |
|---|---|---|---|---|
| ATCC824(pJIR750)_A | 0.72 | 0.40 | 0.51 | 0.47 |
| ATCC824(pJIR750)_B | 1.11 | 0.50 | 0.46 | 0.37 |
| ATCC824(pJIR750-FNR)_A | 1.53 | 0.65 | 0.86 | 1.13 |
| ATCC824(pJIR750-FNR)_B | 1.65 | 0.67 | 1.04 | 1.20 |

TABLE 2 butanol/acetone ratio of wildtype *C. acetobutylicum* with or without FNR from *Chlorobium tepidium*

| Strain | Butanol:Acetone ratio 6 h | 24 h | 48 h | 72 h |
|---|---|---|---|---|
| ATCC824(pJIR750)_A | 14.78 | 1.55 | 1.50 | 1.55 |
| ATCC824(pJIR750)_B | 18.16 | 1.37 | 1.46 | 1.57 |
| ATCC824(pJIR750-FNR)_A | 29.52 | 2.23 | 2.36 | 2.70 |
| ATCC824(pJIR750-FNR)_B | 23.41 | 2.28 | 2.80 | 3.18 |

TABLE 3 butyrate/acetate ratio of pSOL1$^-$ mutant *C. acetobutylicum* with or without FNR from *Chlorobium tepidium*

| Strain | Butyrate:Acetate ratio 6 h | 24 h | 48 h | 72 h |
|---|---|---|---|---|
| M5_A | 1.21 | 2.15 | 2.21 | 2.03 |
| M5_B | 0.93 | 1.61 | 1.85 | 1.71 |
| M5(pJIR750)_A | 1.17 | 1.78 | 1.77 | 1.71 |
| M5(pJIR750)_B | 1.23 | 1.83 | 1.88 | 1.73 |
| M5(pJIR750-FNR)_A | 4.61 | 3.97 | 4.35 | 3.81 |
| M5(pJIR750-FNR)_B | 2.34 | 3.45 | 3.65 | 3.15 |

The following experiment was done in a mutant of *Clostridium acetobutylicum*—PJC4BK—that is disrupted in buk, the gene encoding the major butyrate kinase, and called BUK or buk$^-$ herein. This strain has higher butanol formation than the parent ATCC824 because it is limited for the pathway from butyryl-CoA to butyrate as described in Green (1996). It was used as a host for the same plasmids described above in order to show the effect in a higher solvent forming derivative of *C. acetobutylicum* that already produces a higher level of butanol than the wild type parent.

pJIR750-FNR has a SalI fragment of pSOS94-FNR subcloned into pJIR750. pSOS94-FNR contains codon optimized Ferredoxin NAD(P) reductase of *Chlorobium tepidium* (DNA2.0 construct). pSOS94 is another shuttle vector for *Clostridia*, but the FNR was moved because the pSOS vector and the chromosome of the high solvent producing mutant both carry the MLS drug resistance marker for erythromycin. Thus, the use of a shuttle vector with a different selectable marker was needed.

A single colony from transformation plate (2×YTG agar plate with Thiamphenicol 20 µg/ml) inoculated in 10 mL CGM+ medium containing Th20—18 h at 37° C. (CGM+ is a modified CGM recipe with 50 g/L glucose) 100 µl of preculture inoculated in 10 mL CGM+ in 15 ml tube+ Th20—37° C. for 72 hours. 1 ml sample collected at 6 h, 24 h, 48 h and 72 h—centrifuged, acidified with 20 µL 50% $H_2SO_4$ and ran on GC for metabolites and the results shown in Tables 4-7.

The experimental is as described in the previous examples.

Table 4 shows the addition of the plasmid with the FNR$^+$ does not drastically effect the growth or OD value. The control Buk$^-$JIR750 is with a plasmid alone with no FNR gene in it. The test strain has FNR encoded by the same vector. A and B are two different isolates from the same transformation.

TABLE 4

OD of the cultures Buk$^-$ JIR750 and Buk$^-$ JIR750-FNR$^+$

| Strain | Short name | 6 hr | 24 hr | 48 hr |
|---|---|---|---|---|
| Buk$^-$ JIR750 - A | Control-1 | 0.7 | 12.54 | 11 |
| Buk$^-$ JIR750 - B | Control-2 | 0.6 | 12.16 | 12.4 |
| Buk$^-$ JIR750-FNR$^+$ - A | FNR-1 | 0.5 | 10.64 | 11.6 |
| Buk$^-$ JIR750-FNR$^+$ - B | FNR-2 | 0.5 | 9.12 | 11 |

The metabolite analysis of the fermentation products of the cultures is seen in Table 5, where butanol production is considerably improved.

TABLE 5

Metabolite levels in BUK *Clostridium* with or without FNR
Buk host plus vector alone = control-1 and control 2
Buk(pJIR750-FNR) = FNR-1 & FNR-2

| | mM of metabolite |
|---|---|
| Control-1_48 h | |
| Ethanol | 39.938 |
| Acetone | 47.160 |
| Acetate | 10.382 |
| Butanol | 95.580 |
| Butyrate | 12.730 |
| Control-2_48 h | |
| Ethanol | 39.706 |
| Acetone | 49.680 |
| Acetate | 9.730 |
| Butanol | 97.840 |
| Butyrate | 14.350 |
| FNR-1_48 h | |
| Ethanol | 36.705 |
| Acetone | 30.460 |
| Acetate | 6.080 |
| Butanol | 102.290 |
| Butyrate | 6.220 |
| FNR-2_48 h | |
| ethanol | 33.966 |
| acetone | 33.550 |
| acetate | 5.640 |
| butanol | 104.420 |
| butyrate | 6.590 |

Looking at important ratios for high butanol production processes, the effect of the added enzyme is significant and positive, as seen in Tables 6-8.

TABLE 6

| Solvent/acid ratio metabolite levels in BUK *Clostridium* with or without FNR. The solvents are a total of butanol plus acetone plus ethanol the acids are acetate and butyrate | | |
|---|---|---|
| | 24 h | 48 h |
| Control-1 | 8.533 | 7.904 |
| Control-2 | 8.329 | 7.775 |
| FNR-1 | 12.150 | 13.777 |
| FNR-2 | 11.362 | 14.059 |

TABLE 7

| % Butanol of total solvents (g/L basis) in BUK *Clostridium* with or without FNR | | | |
|---|---|---|---|
| Strains | 24 h | 48 h | 72 h |
| Control-1 | 56.708 | 60.741 | 65.013 |
| Control-2 | 56.82 | 60.6 | 64.136 |
| FNR-1 | 63.687 | 68.664 | 72.274 |
| FNR-2 | 63.494 | 68.778 | 73.057 |

TABLE 8

| Acetone and Butanol with FNR from *C. tepidium* in a BUK background | | | | |
|---|---|---|---|---|
| Strain | Acetone (mM) 72 hrs | Butanol (mM) 72 hrs | Butanol/ acetone 48 hrs | Butanol/ acetone 72 hrs |
| buk pJIR750 | 41.8 | 102 | 2.0 | 2.44 |
| buk pJIR750-FNR | 24.7 | 106 | 3.23 | 4.32 |

The butanol mass proportion is shown in Table 9, and butanol/solvent in Table 10.

TABLE 9

| Butanol mass proportion with FNR from *C. tepidium* in a BUK background | | | |
|---|---|---|---|
| Strain | Butanol as % of total metabolites (g/L) 24 hrs | Butanol as % of total metabolites (g/L) 48 hrs | Butanol as % of total metabolites (g/L) 72 hrs |
| buk pJIR750 | 51.6 | 54.3 | 58.3 |
| buk pJIR750-FNR | 60.8 | 65.8 | 69.9 |

TABLE 10

| Butanol mass solvent proportion with FNR from *C. tepidium* in a BUK background | | | |
|---|---|---|---|
| Strain | Butanol as % of total solvents (g/L) 24 hrs | Butanol as % of total solvents (g/L) 48 hrs | Butanol as % of total solvents (g/L) 72 hrs |
| buk pJIR750 | 59.3 | 62.6 | 66.9 |
| buk pJIR750-FNR | 66.8 | 71.4 | 75.5 |

These experiments show that the proportion of butanol and butyrate is increased in the presence of the FNR gene encoded by *C. tepidium.*

Although one might predict that any enzyme that reduces NAD to NADH could be used herein, our experimental work shows this is not in fact so. TER uses NADH directly to reduce the crotonyl-CoA to butyryl-CoA and has been used in *E. coli* to make butanol. However, our results show that it will not function as intended herein.

A different TER was tested and also found to be non-functional, suggesting that the above result is generally applicable. The gene coding for the *T. denticola* enzyme (Acc. No. NP_971211.1) was synthesized, expression optimized by DNA2.0, cloned into the vector pJIR750 and transformed into *C. acetobutylicum* M5 (a non-solvent producing strain) so acetate vs butyrate can be examined. Table 11 shows a reduction of butyrate, rather than an improvement.

TABLE 11

| Acetate and Butyrate with TER from *Treponema denticola* in pSOL⁻ background | | | |
|---|---|---|---|
| STRAIN | Acetate MM 24 HR | Butyrate (mM) 24 hr | butyrate/acetate ratio 24 hr |
| M5 pJIR750 OD = 5.5 | 24.9 | 44.7 | 1.8 |
| M5 pJIR750-TER OD = 5.9 | 22.4 | 33.5 | 1.5 |
| | Acetone (mM) 72 hrs | Butanol (mM) 72 hrs | butanol/acetone ratio 72 hr |
| M5 pJIR750 | 47.8 | 74.7 | 1.56 |
| M5 pJIR750-TER | 25.8 | 49.4 | 1.91 |

The TER experiments were another way of doing the NADH utilization as this enzyme reduced the crotonyl-CoA to butyryl-CoA with just NADH rather than the Clostridial enzyme that uses NADH and oxidized Fd and gives butyryl-CoA and reduced Fd and NAD in a more complex bifurcating reaction. It was synthesized and expressed in the same way as the FNR enzyme, but it had a lowering effect on the butyrate and butanol in the way it was expressed and tested. These negative results suggest that the minimum requirement for functionality hereunder is addition of extra ferredoxin NAD(P)H reductase activity. We did not test TER in the presence of FNR to see if the coupled system had a positive effect.

Each of the following citations is incorporated by reference herein in its entirety for all purposes:

Cai, X., et al., 2013. Analysis of redox responses during TNT transformation by *Clostridium acetobutylicum* ATCC 824 and mutants exhibiting altered metabolism. Appl Microbiol Biotechnol. 97(10):4651-4663.

Calusinska, M., et al., 2010. The surprising diversity of clostridial hydrogenases: a comparative genomic perspective. Microbiology. 156(6): 1575-1588.

Clark, S. W., at al., 1989. Isolation and characterization of mutants of *Clostridium acetobutylicum* ATCC 824 deficient in acetoacetyl-coenzyme A:acetate/butyrate:coenzyme A-transferase (EC 2.8.3.9) and in other solvent pathway enzymes. Appl. Environ Microbiol. 55 (4): 970-976.

Frigaard, N. U., et al., 2003. *Chlorobium tepidum*: insights into the structure, physiology, and metabolism of a green sulfur bacterium derived from the complete genome sequence. Photosynth Res. 78(2):93-117.

Girbal, L., et al., 2005. Homologous and heterologous overexpression in *Clostridium acetobutylicum* and characterization of purified clostridial and algal Fe-only hydrogenases with high specific activities. Appl. Environ Microbiol. 71(5):2777-2781.

Green, E. M., et al., 1996. Genetic manipulation of acid formation pathways by gene inactivation in *Clostridium acetobutylicum* ATCC 824, Microbiology, 142, 2079-2086.

Hillmann F, et al., 2008. PerR acts as a switch for oxygen tolerance in the strict anaerobe *Clostridium acetobutylicum*, Mol Microbiol. 68(4):848-60.

Hurley J. K., et al., 2002. Structure-function relationships in *Anabaena* ferredoxin/ferredoxin:NADP(+) reductase electron transfer: insights from site-directed mutagenesis, transient absorption spectroscopy and X-ray crystallography, Biochim Biophys Acta. 1554(1-2):5-21.

Peters, J. W., et al., 1998. X-ray crystal structure of the Fe-only hydrogenase (CpI) from *Clostridium pasteurianum* to 1.8 angstrom resolution. Science. 282(5395): 1853-1858.

Peregrina J. R., et al., 2009. Motifs involved in coenzyme interaction and enzymatic efficiency in *anabaena* ferredoxin-NADP+ reductase. Biochemistry. 2009 48(14): 3109-19.

Seo, D., Sakurai, H. 2002. Purification and characterization of ferredoxin-NAD(P)(+) reductase from the green sulfur bacterium *Chlorobium tepidum*. Biochim Biophys Acta. 1597 (1):123-132.

Seo, D., et al., 2001. Purification of ferredoxins and their reaction with purified reaction center complex from the green sulfur bacterium *Chlorobium tepidum*. Biochim Biophys Acta. 1503(3):377-384.

Tejero J. et al., 2003. Involvement of the pyrophosphate and the 2'-phosphate binding regions of ferredoxin-NADP+ reductase in coenzyme specificity, J Biol Chem. 278(49): 49203-14.

Wagner C., et al., 1996. Acetogenic capacities and the anaerobic turnover of carbon in a kansas prairie soil, Appl. Environ. Microbiol. 62(2): 494-500.

Watrous, M. M., et al., 2003. 2,4,6-trinitrotoluene reduction by a Fe-only hydrogenase in *Clostridium acetobutylicum*. Appl. Environ Microbiol. 69(3):1542-1547.

Yoon, K. S., et al., 2001. Spectroscopic and functional properties of novel 2[4Fe-4S] cluster-containing ferredoxins from the green sulfur bacterium *Chlorobium tepidum*. J. Biol. Chem. 276(47):44027-44036.

Shen et al. 2011. Driving forces enable high-titer anaerobic 1-butanol synthesis in *Escherichia coli*. Appl Environ Microbiol. 77(9):2905-15.

---

The invention claimed is:

1. A method for the bioproduction of a C4+ compound, said method comprising: a. anaerobically growing a bacteria in a culture medium comprising a carbon source; b. conversion of said carbon source to a C4+ compound; and c. purification of said C4+ compound, said bacteria being a genetically engineered bacteria comprising an overexpressed ferredoxin-NAD(P)+ reductase (FNR) capable of catalyzing reduction of either NADP+ or NAD+ or both, said bacteria able to anaerobically produce more C4-8 organic acids or alcohols than a similar bacteria lacking said overexpressed FNR.

2. The method of claim 1, wherein said C4+ compound is butyrate, butanol, valeric acid, pentanol, hexanoate, hexanol, heptanoate, heptanol, octanoate, octanol, or a derivative thereof.

3. The method of claim 1, wherein said C4+ compound is butyrate.

4. The method of claim 1, wherein said C4+ compound is butanol.

5. The method of claim 1, wherein said growing step is anaerobic.

6. The method of claim 1, wherein said growing step is 100% anaerobic.

7. The method of claim 1, wherein said growing step is <100% anaerobic.

8. The method of claim 1, wherein said FNR is a heterologous FNR.

9. The method of claim 1, said bacteria further comprising a mutation such that said bacteria cannot make lactate.

10. The method of claim 1, wherein said bacteria is an acetogenic bacteria.

11. The method of claim 1, wherein said bacteria is a *Clostridium, Clostridium acetobutylicum, Clostridium acetobutylicum M5, Clostridium thermocellum, Clostridium ljungdahlii, Clostridium thermoautotrophicum,* or *Clostridium tyrobutyricum.*

12. The method of claim 1, wherein said bacteria is a *Butyrobacterium, Moorella thermoacetica, Sporomusa, Thermacetogenium phaeum, Acetogenium kivui, Acetobacterium woodii,* or *Eubacterium.*

13. The method of claim 10, said bacteria further comprising a mutation such that said bacteria cannot make acetone.

14. The method of claim 10, said bacteria further comprising a mutation such that said bacteria cannot make lactate.

* * * * *

SEQUENCE LISTING

```
<160> NUMBER OF SEQ ID NOS: 3

<210> SEQ ID NO 1
<211> LENGTH: 360
<212> TYPE: PRT
<213> ORGANISM: Chlorobium tepidum

<400> SEQUENCE: 1

Met Leu Asp Ile His Asn Pro Ala Thr Asp His His Asp Met Arg Asp
1               5                   10                  15

Leu Thr Ile Ile Gly Gly Gly Pro Thr Gly Ile Phe Ala Ala Phe Gln
            20                  25                  30

Cys Gly Met Asn Asn Ile Ser Cys Arg Ile Ile Glu Ser Met Pro Gln
        35                  40                  45

Leu Gly Gly Gln Leu Ala Ala Leu Tyr Pro Glu Lys His Ile Tyr Asp
    50                  55                  60

Val Ala Gly Phe Pro Glu Val Pro Ala Ile Asp Leu Val Glu Ser Leu
65                  70                  75                  80

Trp Ala Gln Ala Glu Arg Tyr Asn Pro Asp Val Val Leu Asn Glu Thr
                85                  90                  95

Val Thr Lys Tyr Thr Lys Leu Asp Asp Gly Thr Phe Glu Thr Arg Thr
            100                 105                 110

Asn Thr Gly Asn Val Tyr Arg Ser Arg Ala Val Leu Ile Ala Ala Gly
        115                 120                 125

Leu Gly Ala Phe Glu Pro Arg Lys Leu Pro Gln Leu Gly Asn Ile Asp
    130                 135                 140

His Leu Thr Gly Ser Ser Val Tyr Ala Val Lys Ser Val Glu Asp
145                 150                 155                 160

Phe Lys Gly Lys Arg Val Val Ile Val Gly Gly Gly Asp Ser Ala Leu
                165                 170                 175

Asp Trp Thr Val Gly Leu Ile Lys Asn Ala Ala Ser Val Thr Leu Val
            180                 185                 190

His Arg Gly His Glu Phe Gln Gly His Gly Lys Thr Ala His Glu Val
        195                 200                 205
```

-continued

```
Glu Arg Ala Arg Ala Asn Gly Thr Ile Asp Val Tyr Leu Glu Thr Glu
        210                 215                 220
Val Ala Ser Ile Glu Glu Ser Asn Gly Val Leu Thr Arg Val His Leu
225                 230                 235                 240
Arg Ser Ser Asp Gly Ser Lys Trp Thr Val Glu Ala Asp Arg Leu Leu
                245                 250                 255
Ile Leu Ile Gly Phe Lys Ser Asn Leu Gly Pro Leu Ala Arg Trp Asp
            260                 265                 270
Leu Glu Leu Tyr Glu Asn Ala Leu Val Val Asp Ser His Met Lys Thr
        275                 280                 285
Ser Val Asp Gly Leu Tyr Ala Ala Gly Asp Ile Ala Tyr Tyr Pro Gly
290                 295                 300
Lys Leu Lys Ile Ile Gln Thr Gly Leu Ser Glu Ala Thr Met Ala Val
305                 310                 315                 320
Arg His Ser Leu Ser Tyr Ile Lys Pro Gly Glu Lys Ile Arg Asn Val
                325                 330                 335
Phe Ser Ser Val Lys Met Ala Lys Glu Lys Ala Ala Glu Ala Gly
            340                 345                 350
Asn Ala Thr Glu Asn Lys Ala Glu
        355                 360
```

<210> SEQ ID NO 2
<211> LENGTH: 1080
<212> TYPE: DNA
<213> ORGANISM: Clostridium acetobutylicum

<400> SEQUENCE: 2

```
atgttagata tccataatcc agcaaccgac caccatgata tgagagattt gactattatc      60
ggcggtggtc cgaccgggat atttgctgcc tttcaatgtg gtatgaataa catatcatgc    120
agaatcattg aatctatgcc tcaattgggt ggtcaacttg ctgcactata tccagaaaaa    180
catatctatg acgttgcagg atttcccgaa gttccagcta ttgatttggt tgagtcatta    240
tgggcacaag cggaaagata aacccagat gtcgtcctta atgaaacagt aaccaagtat    300
accaaattag acgatgggac gtttgagact agaaccaata caggtaatgt ttatcgatca    360
agagctgtac ttattgcagc gggattagga gcatttgaac cacgtaaact tccccaatta    420
ggcaatatag atcatctaac cggtagttct gtatactatg cggttaaaag cgttgaagat    480
ttcaaaggta aagagttgt tatagtcggt ggtggagaca cgcgcttaga ctggaccgtc    540
ggacttatca aaatgctgc atcagtaaca ttagtgcaca gaggacatga atttcaaggt    600
catggtaaaa ccgcccatga gtggaaaga gcaagagcta atggtactat tgatgtgtat    660
ttggaaacag aggtagcaag cattgaagag tctaatggag tattaactag agttcatctt    720
agatcaagtg acggttcaaa gtggactgtt gaagcggata gacttcttat tctaataggt    780
tttaagtcaa acttaggtcc tttagcaaga tgggatttag aactttatga aaatgcttta    840
gttgttgatt ctcacatgaa aacttccgtt gacggacttt atgctgcagg agacattgca    900
tattacccgg ggaaattgaa aatcatacag actgggttat cagaagcgac tatggctgta    960
aggcattccc ttagttatat caaacctggt gagaaaatac gtaacgtgtt cagttccgtc   1020
aagatggcga agaaaagaa agccgcagaa gctgggaatg ctactgagaa taaggctgag   1080
```

<210> SEQ ID NO 3
<211> LENGTH: 14
<212> TYPE: DNA
<213> ORGANISM: Artificial Sequence

```
<220> FEATURE:
<223> OTHER INFORMATION: Ribosome binding site

<400> SEQUENCE: 3
aggaggtaaa acat                                                        14
```